United States Patent [19]

Langley

[11] Patent Number: 4,847,393

[45] Date of Patent: Jul. 11, 1989

[54] PROCESS FOR THE PRODUCTION OF ETHYLENE OXIDE

[75] Inventor: Philip Langley, Cleveland, England

[73] Assignee: Imperial Chemical Industries PLC, London, United Kingdom

[21] Appl. No.: 86,602

[22] Filed: Aug. 18, 1987

[30] Foreign Application Priority Data

Aug. 29, 1986 [GB] United Kingdom ............... 8620970
Aug. 29, 1986 [GB] United Kingdom ............... 8620971

[51] Int. Cl.$^4$ .................. C07D 301/08; C07D 301/10
[52] U.S. Cl. .................................. 549/523; 549/534; 549/536; 549/537; 549/538
[58] Field of Search ............... 549/523, 534, 536, 537, 549/538

[56] References Cited

U.S. PATENT DOCUMENTS

| | | | |
|---|---|---|---|
| 1,995,991 | 3/1985 | Lehner | 549/523 |
| 3,145,220 | 8/1964 | Bartok | 549/523 |
| 3,335,547 | 8/1967 | Garrett | 55/75 |
| 3,483,229 | 12/1969 | Bernard | 549/523 |
| 4,376,209 | 3/1983 | Watanabe et al. | 549/534 |

*Primary Examiner*—Asok Pal
*Attorney, Agent, or Firm*—Cushman, Darby & Cushman

[57] ABSTRACT

In a process of producing ethylene oxide by contacting ethylene and oxygen with a main body of a solid catalyst in a reaction zone and passing product from that zone through a substantial volume to a cooler, acetaldehyde is produced by isomerization of ethylene oxide in the volume. The acetaldehyde content of the gases entering the cooler is reduced in this invention by passing them through a second, smaller bed of catalyst before the gases are passed to the cooler.

6 Claims, 1 Drawing Sheet

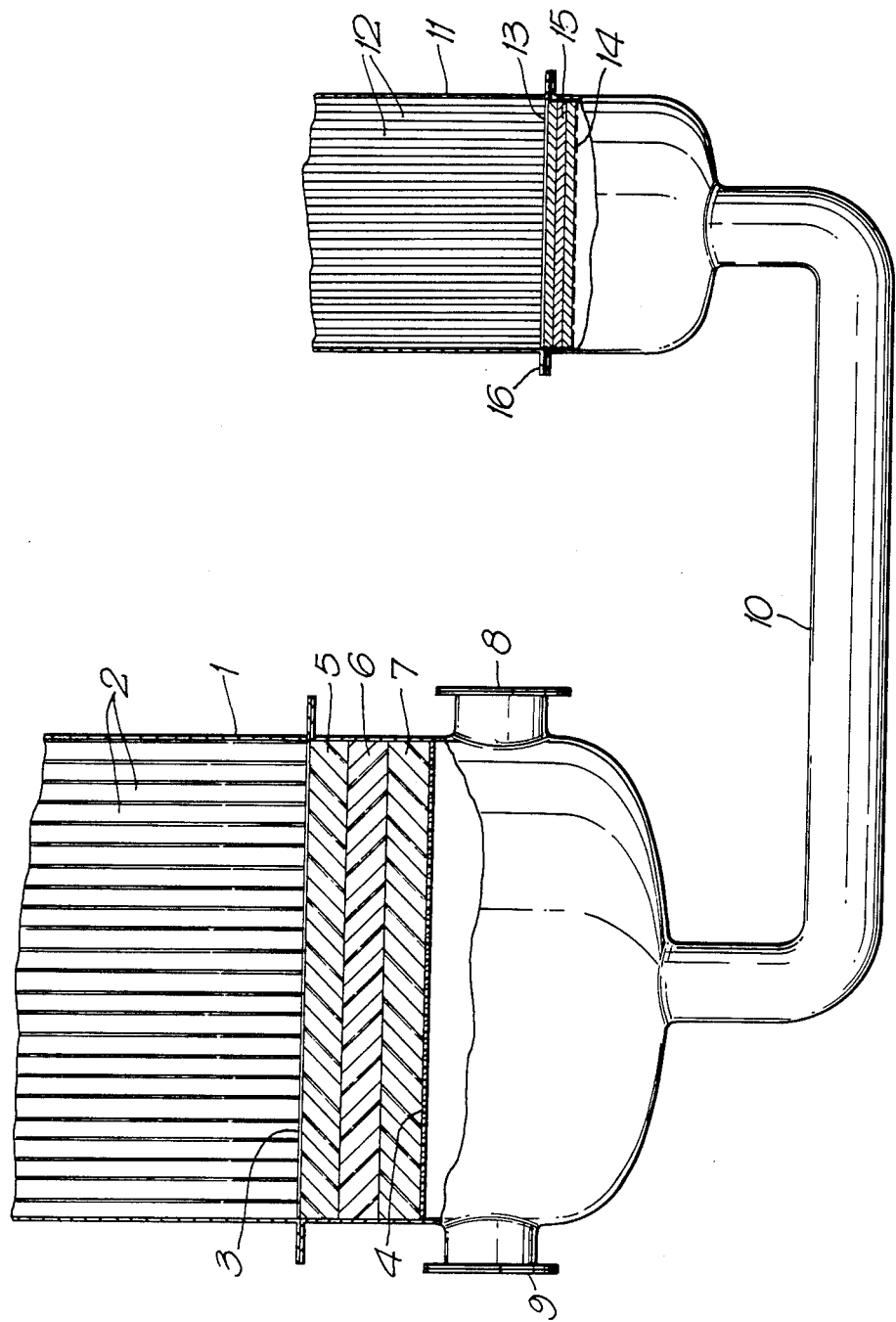

PROCESS FOR THE PRODUCTION OF ETHYLENE OXIDE

This invention relates to a process for the production of ethylene oxide.

Ethylene oxide is commonly produced by passing ethylene, oxygen and other gases usually including a chlorine containing reaction inhibitor, for example ethylene dichloride or vinyl chloride, through a bed of a suitable catalyst which usually comprises silver on a heat resistant support, for example an α-alumina support. The catalyst may be packed in the tubes of a tubular reactor, the outside of the tubes being contacted with a heat exchange fluid to control the temperature in the tubes.

Where the gases emerge from the reactor tubes it may be desirable or necessary for mechanical reasons to pass them through a volume of empty or packed space before they are cooled. This may arise for example if the gases are passed from a reactor to a separate cooler, the volume of space in this case comprising any free space in the reactor beyond the reactor tubes, in the pipework and possibly space in the cooler before any cooing tubes. During passage through this space the gases are hot and ethylene oxide tends to isomerise to acetaldehyde, which is difficult to remove from ethylene oxide and may thus contaminate the product.

This invention comprises a process of producing ethylene oxide by contacting ethylene and oxygen with a main body of a solid catalyst in a reaction zone, recovering a gaseous reaction product from the said zone and passing it at a temperature at which isomerisation of ehtylene oxide to acetaldehyde is significant through a substantial volume to a cooler, characterised in that the acetaldehyde content of the gaseous reaction product is decreased after passage through a substantial part of the said volume by passing it through a second, smaller bed of a catalyst for the oxidation of ethylene with oxygen to ethylene oxide and then cooling it.

The main body of catalyst is suitably a fixed bed packed into a tubular reactor.

Combustion of ethylene and/or other gases present with the oxygen may occur if the concentration of the oxygen is too high. Whereas this can readily be controlled at the inlet to the reactor tubes and to a lesser extent, by ensuring as far as possible that the tubes are homogeneous when they are first filled with catalyst, at their outlets, we have found that despite operating at oxygen levels which should allow an ample safety factor such combustion can nonetheless occasionally occur at the outlet of the reactor tubes.

This tends to occur after the catalyst has been used for some time and we believe (though we do not wish to be bound by the following explanation) that it is associated with a faster rate of decay of catalyst in some tubes that in others. This, we believe, leads to less oxygen being consumed in such tubes. Because the general rise in temperature of gases in the reaction lowers the flammable limit for oxygen, the effluent from tubes with decayed catalyst injects an excess of oxygen into the hot gases emerging from other tubes and leads to combustion.

In a further aspect of this invention this difficulty is reduced by rapidly mixing the effluent from the main reactor tubes transversely in the presence of inert packing.

Thus at least some, and if desired all, of the said substantial volume may be occupied by inert packing.

It is known from U.S. Pat. No. 4,051,659 to cool the product of the ethylene oxide reaction in the presence of inert refractory particulate material to reduce the isomerisation of ehtylene oxide to acetaldehyde and U.S. Pat. No. 4,376,209 contains similar teaching in which the particulate material contains for example calcium, strontium or barium to inhibit isomerisation futher. Such procedures may be used in this invention but any substantial cooling of the gas is physically difficult to combine with a simultaneous effective immediate transverse admixture of gases emerging from the catalyst tubes which is desirable to avoid combustion.

The means for transverse mixing may take the form of cooling tubes or cooled baffles, but any means intended to cool the gases during the transverse mixing tends to increase the volume of the mixing zone and thus to delay mixing, and to increase back pressure and we prefer therefore to carry out the mixing without substantial cooling. As acetaldehyde produced by isomerisation during mixing will be consumed in the second bed of catalyst, the lack of cooling is acceptable.

Whilst a bed of appropriately shaped and ordered inert inorganic refractory particles might be used to cause transverse mixing, normal particles produce a somewhat random packing in beds. The lateral, transverse flow leading to mixing tends to be modest compared with the direction of the flow of the gas stream taken as a whole in randomly packed beds. We prefer therefore to use packing having a more ordered structure adapted to increase the transverse mixing above the levels occurring with beds of randomly packed particles of the normal pelletted type (spheres, rings, cylinders, etc) or random shaped (eg fractured) particles. We therefore prefer to use packing elements which have an ordered structure, which may be made for example of metal or ceramic material and which impart a greater transverse mixing effect. Packing elements of this type used in distillation, for example the metal or ceramic elements described by W Meyer in the Sulzer Technical Review 2/1979 pages 49 onward may be used. It will be appreciated that the materials used should be temperature and oxygen resistant and should not catalyse undesired side reactions.

During passage through the second bed more ethylene oxide may also be formed.

The catalyst may be of conventional type, for example it may comprise 3% to 30% and preferably 5 to 20% by weight of silver on a porous heat resisting support, for example an alpha alumina support suitably having a surface area of 0.05 to 10 for example 0.1 to 2 and preferably 0.2 to 1 $m^2/g$ and optionally containing an alkali metal for example sodium, potassium, rubidium and/or cesium in a form which may be removed and may conveniently be similar or identical to that of the main body.

The temperatures at which isomerisation of ethylene oxide to acetaldehyde becomes a significant problem are 180° to 300° C.

Cooling preferably takes place immediately after passage through the second bed. It may conveniently take place in a conventional heat exchanger.

The process of producing ethylene oxide may be conventional, and is normally carried out in the presence of a small quantity of a chlorine containing reaction inhibitor, for example vinyl chloride or ethylene dichloride, for example, at a temperature of 200°–300°

C. and a pressure of 0.5 to 30 bars absolute and very suitable is carried out also in the presence of a compound in the gas phase which is capable of forming nitrate and/or nitrite ions in the catalyst as disclosed in our British Pat. No. 2,014,133.

EXAMPLE 1

56g of a commercial catalyst comprising silver on an α-alumina support was ground to 1-3 mm diameter particles and charged to a 11 mm internal diameter stainless steel reactor tube giving 75 cm bed length. 270l/hr of gas comprising 30% $C_2H_4$, 8% $O_2$, 2.5% $CO_2$, 3.5 ppm vinyl chloride, 0.5 ppm ethyl chloride, 0.05% $C_2H_6$, the balance being nitrogen were passed over the catalyst at 225° C. at 16 bar pressure giving 29.2% oxygen conversion and a selectivity of $C_2H_4$ to ethylene oxide of 81.2%. Downstream of the catalyst bed was 50 cm of empty tube at the same temperature and pressure as above. The aldehyde content of the exit gas after cooling was 4.3ppm. When a 1 cm length bed of the same catalyst was inserted at the end of the empty tube the exit aldehyde content was found to be 2.4 ppm after subsequent cooling.

EXAMPLE 2

82 g of a used commercial catalyst comprisisng silver on an α-alumina support was ground to 1-3 mm diameter particles and charged to a 11 mm internal diameter stainless steel reactor tube giving 79 cm bed length. 285 l/hr of gas comprising 30% $C_2H_4$, 8% $O_2$, 2.5% $CO_2$, 3.5 ppm vinyl chloride, 0.5 ppm ethyl chloride, 0.05% $C_2H_6$, the balance being nitrogen was passed over the catalyst at 255° C. at 16 bar pressure giving 33.8% oxygen conversion and selectivity of $C_2H_4$ to ethylene oxide of 77.9%. Downstream of the catalyst bed was 50 cm of empty tube at the same temperature and pressure as above. The aldehyde content of the exit gas after cooling was 9.5 ppm. When 2 g of the same catalyst was inserted at the end of the empty tube, the exit aldehyde content was found to be 4.6 ppm after subsequent cooling. ppm means parts per million gas. gas concentration are by volume.

One form of the invention embodying transverse mixing of reactor effluent will now be described with reference to the accompanying drawing which shows a schematic view of the lower part of an ethylene oxide reactor and of a cooler 11.

p BRIEF DESCRIPTION OF THE DRAWINGS

The upper part of the reactor 1 comprises externally cooled tubes 2 which are packed with a supported silver catalyst and end in a tube plate 3. To the underside of the tube plate 3 is secured by bolts (not shown) a perforated plate 4 supporting packing material sold under the trade name Mellapack by Sulzer. This comprises three layers of corrugated metal sheets 5, 6, and 7 each layer arranged as parallel packs lying at 45° to the vertical, thus connecting rows of reactor tube outlets, each layer being oriented with respect to the one below as rotated about the axis of the reactor through 90° thus connecting the said rows of reactor tube outlets to other rows and thereby mixing effluent from the tubes more thoroughly.

Access is provdied for the installation of the packing through manholes 8 and 9. For convenience of installation the packing and the support plate 4 are made as abutting sections which sections can be passed through the manholes and assembled in situ.

The mixed gases pass from reactor 1 through pipe 10 to cooler 11 which comprises tubes 12 through which the gases are passed. They are cooled externally with a heat exchange fluid and end in a tube plate 13 to the under surface of which is held a layer of catalyst 15 identical to that in reactor 1 by means of perforated plate 14 which is bolted to the tube plate 13. The cooler is of smaller size than the reactor 1 and consequently access to bed 15 can be readily obtained by disconnecting flanges 16 of the cooler and lifting the upper part of it clear. The reactor bed 15 is about 2.5% of the volume of the bed in reactor 1.

In operation a gas stream comprising 30% ethylene, 7.5% oxygen, 6% $CO_2$, 2 ppm vinyl chloride, 0.5 ppm ethyl chloride, the balacne being largely methane and ineerts with some ethane is passed through the tubes of reactor 1 at an inlet temperature of 140° C. and an outlet temperature of 260° C. giving an average oxygen conversion of about 40% at a selectivity of ethylene to ethylene oxide of about 75.

Any non uniformity of conversion of oxygen in different reactor tubes is compensated by the rapid mixing of the gases from different tubes in packing layers 5, 6 and 7. The gases then pass to cooler 11 in which catalyst bed 15 serves to oxidise at least part of any acetaldehyde formed by isomerisation of ethylene oxide in the space between tubes 2 and bed 15, immediately before the gases are cooled. ppm means parts per milion. gas concentrations are by volume.

I claim:

1. In a process of producing ethylene oxide by contacting ethylene and oxygen with a main body of a solid catalyst in a reaction zone, recovering a gaseous reaction product from the said zone and passing the gaseous reaction product to a cooler, the improvement which comprises passing the gaseous reaction product after its recovery from said reaction zone but before passing it to the cooler through a second, smaller bed of a catalyst for the oxidation of ethylene with oxygen to ethylene oxide whereby the acetaldehyde content of the reaction product is decreased before the reaction product enters the cooler.

2. A process as claimed in claim 1, in which the main body of catalyst is a fixed bed packed in a tubular reactor.

3. A process as claimed in claim 2 in which the outlets of the tubes of the tubular reactor feed into a zone in which gases emerging from the tubes are rapidly mixed transversely by contact with solids.

4. A process as claimed in claim 3 in which the gases are mixed transversely without substantial cooling.

5. A process as claimed in claim 4 in which the gases are mixed transversely using packing elements of metal or ceramic material which have an ordered structure.

6. A process as claimed in claim 1 in which the second bed of catalyst is 0.5% to 5% of the volume of the first bed.

* * * * *